(12) United States Patent
Lannuzel et al.

(10) Patent No.: US 6,255,520 B1
(45) Date of Patent: Jul. 3, 2001

(54) ORGANIC SOLUTION OF DIALKYL PEROXYDICARBONATE AND PROCESS FOR PRODUCING THEREOF

(75) Inventors: Thierry Lannuzel, Ta vaux (FR); Vincent Bodart, Namur (BE); Xavier Bacque, Tauvaux (FR); Guy Laurent, Vedrin (BE); Fredy Declerck, Grimbergen (BE)

(73) Assignee: Solvay (Societe Anonyme), Brussels (BE)

( * ) Notice: Subject to any disclaimer, the term of this patent is extended or adjusted under 35 U.S.C. 154(b) by 0 days.

(21) Appl. No.: 09/120,395

(22) Filed: Jul. 22, 1998

(30) Foreign Application Priority Data

Jul. 22, 1997 (BE) .................................................. 09700633

(51) Int. Cl.$^7$ ................................ C08F 4/36; C08F 4/02
(52) U.S. Cl. ........................................... 558/264; 502/160
(58) Field of Search .............................. 558/264; 502/160

(56) References Cited

U.S. PATENT DOCUMENTS 4,524,194   6/1985   Dumoulin ............................. 526/84

FOREIGN PATENT DOCUMENTS 1 055 985   1/1967   (GB) .
1 484 675   9/1977   (GB) .

OTHER PUBLICATIONS

Derwent Publication Ltd., London, GB; Class A14, AN 87–155165, RO 90 603, Nov. 29, 1986.

Patent Abstracts of Japan, vol. 18, No. 122 (C–1173), Feb. 28, 1994, JP 05/310 915.

*Primary Examiner*—Fiona T. Powers
(74) *Attorney, Agent, or Firm*—Kate H. Murashige; Morrison & Foerster LLP

(57) ABSTRACT

The invention relates to a process for the preparation of an organic solution of dialkyl peroxydicarbonate which is particularly suited for use in the aqueous suspension polymerization of halogenated monomers. According to this process, the dialkyl peroxydicarbonate, prepared by the reaction in water of appropriate amounts of alkyl haloformate with an inorganic peroxide, is separated by extraction by means of a water-insoluble organic solvent chosen from conventional chain-regulating agents for halogenated polymers.

8 Claims, No Drawings

ORGANIC SOLUTION OF DIALKYL PEROXYDICARBONATE AND PROCESS FOR PRODUCING THEREOF

The present invention relates to organic solutions of dialkyl peroxydicarbonate and to their use in the polymerization of halogenated monomers for the purpose of obtaining polymers with improved properties.

It is known to resort to dialkyl peroxydicarbonates in order to initiate the aqueous suspension polymerization of halogenated monomers. Dialkyl peroxydicarbonates are particularly valued initiators because of their high activity at the usual polymerization temperatures. However, they exhibit the disadvantage of being unstable, so that their storage in the pure state exhibits very serious safety risks.

For the purpose of overcoming this disadvantage, provision has already been made to manufacture these dialkyl peroxydicarbonates in the polymerization reactor ("in situ"). This "in situ" preparation process does not, however, make possible automation of the feeding of the polymerization reactors with initiator. In addition, this process lacks reproducibility due to the lack of accuracy with respect to the amounts of initiator effectively employed in the polymerization. This process also lacks productivity because it is necessary to precede each polymerization cycle by the "in situ" synthesis of the initiator. Furthermore, the by-products and residues from the synthesis of the dialkyl peroxydicarbonate are not removed.

Provision has also already been made to prepare the exact necessary amount of dialkyl peroxydicarbonate outside the polymerization reactor ("ex situ") and immediately before the polymerization. This preparation is carried out by reaction of an alkyl haloformate with a peroxide compound in the presence of water and of a volatile water-immiscible solvent preferably having a boiling temperature of less than 100° C. The combined reaction mixture in which the dialkyl peroxydicarbonate has been prepared (aqueous phase and organic phase) is then introduced into the polymerization reactor, which is subsequently charged for the purpose of the polymerization (Belgian Patent 822,913 on behalf of Solvay and Co.). The volatile solvent is preferably removed, in all or in part, before the polymerization by applying vacuum.

This process makes it possible to automate the feeding of the polymerization reactors with initiator but still requires that the exact sufficient amount of initiator be produced immediately before the polymerization. A delayed introduction of the initiator, which is an advantageous technique, for example for improving the kinetics of the polymerization, cannot consequently be carried out. Furthermore, this process does not make it possible to have available a dialkyl peroxydicarbonate solution which can be stored in complete safety and which can be used at any time. Furthermore, the water-soluble impurities present in the aqueous phase after the preparation of the dialkyl peroxydicarbonate are not removed before the introduction into the polymerization reactor.

In order to overcome the disadvantages exhibited by the processes of the prior art, the object of the present invention is to provide an organic solution of dialkyl peroxydicarbonate and more particularly of diethyl peroxydicarbonate which is particularly suited to the preparation of halogenated polymers and more particularly of polymers comprising fluorine (including vinylidene fluoride polymers) by aqueous suspension polymerization and an improved process for manufacturing it.

Another subject-matter of the invention is a simple and efficient process for the preparation of halogenated polymers and more particularly of polymers comprising fluorine (including vinylidene fluoride polymers) by aqueous suspension polymerization with the involvement of this organic solution.

Another subject-matter of the invention is the halogenated polymers and more particularly the polymers comprising fluorine (including vinylidene fluoride polymers) thus obtained.

The present invention first of all relates to an improved process for the preparation of an organic solution of dialkyl peroxydicarbonate, which solution is particularly suited for use in the aqueous suspension polymerization of halogenated monomers.

To this end, the invention relates to a process for the preparation of an organic solution of dialkyl peroxydicarbonate according to which an alkyl haloformate is reacted, in water, in appropriate amounts with an inorganic peroxide and the dialkyl peroxydicarbonate obtained is separated by extraction by means of a water-insoluble organic solvent chosen from conventional chain-regulating agents for halogenated polymers, in order to obtain a solution of dialkyl peroxydicarbonate in this solvent.

The water-insoluble organic solvent is preferably chosen from conventional chain-regulating agents for polymers comprising fluorine and, in a more than preferred way, it is chosen from conventional chain-regulating agents for vinylidene fluoride polymers. In a very particularly preferred way, the water-insoluble organic solvent is diethyl carbonate.

The dialkyl peroxydicarbonate is preferably diethyl peroxydicarbonate.

The alkyl haloformate is generally advantageously an alkyl chloroformate. The inorganic peroxide is generally calcium or sodium peroxide or alternatively hydrogen peroxide. In the latter case, it is advisable, in addition, to introduce a base, such as calcium hydroxide or sodium hydroxide, into the aqueous reaction mixture. Preferably, the inorganic peroxide is hydrogen peroxide and sodium hydroxide is then added to the reaction mixture.

The amount of hydrogen peroxide is usually less than or equal to the stoichiometric amount. It is generally greater than or equal to a stoichiometric shortage of 5% with respect to the amount of alkyl haloformate. The amount of sodium hydroxide is usually less than or equal to the stoichiometric amount. It is generally greater than or equal to a stoichiometric shortage of 5% with respect to the amount of alkyl haloformate. The stoichiometric shortage does not necessarily have to be the same for the hydrogen peroxide and the sodium hydroxide. A stoichiometric shortage of 3% for the sodium hydroxide and of 4% for the hydrogen peroxide with respect to the amount of alkyl haloformate usually gives good results.

The reaction between the alkyl haloformate, hydrogen peroxide and sodium hydroxide is usually carried out with vigorous stirring. The temperature of the reaction is generally maintained at a value between −5° C. and +15° C., preferably between 0° C. and +15° C. The total duration of the preparation of the dialkyl peroxydicarbonate is regulated by the duration of the addition of the sodium hydroxide to the aqueous mixture containing the alkyl haloformate and the hydrogen peroxide, which usually varies from a few tens of minutes to a few hours.

The separation by extraction of the dialkyl peroxydicarbonate obtained is carried out in any known and appropriate way. Advantageously, the extraction solvent is added with vigorous stirring to the aqueous reaction mixture from the preparation of the dialkyl peroxydicarbonate, the phases are subsequently allowed to separate by settling, after the stirring has been halted, and the organic phase is separated from the aqueous phase, in order to collect a pure solution of the dialkyl peroxydicarbonate in the extraction solvent.

The extraction solvent can be added to the aqueous reaction mixture at any point in the reaction for formation of the dialkyl peroxydicarbonate, that is to say from the point ranging from the introduction of the main reactants to after the synthesis of the dialkyl peroxydicarbonate. Furthermore, the extraction solvent can be added all at once or in several steps.

The amount of solvent used for the extraction is not critical. It is obvious that it will depend in particular on the degree of solubility of the dialkyl peroxydicarbonate in the chosen solvent. This amount will advantageously be such that the final concentration of dialkyl peroxydicarbonate in the organic solution is comprised between approximately 15 and approximately 40% by weight and more particularly between approximately 20 and between 35% by weight.

In the case where the relative density of the final aqueous phase after formation of the dialkyl peroxydicarbonate is less than 1.05, it is then necessary to densify the aqueous phase by the addition of a water-soluble inorganic salt in an amount sufficient to increase the relative density of the aqueous reaction mixture and consequently to facilitate the settling and the separation of the aqueous and organic phases.

The inorganic salt is then employed in an amount sufficient to bring the relative density of the aqueous reaction mixture to a value greater than the relative density of the organic solution produced in the second phase. The relative density of the aqueous phase is preferably at least equal to 1.05 and more particularly still to a value at least equal to 1.06. Furthermore, it is advisable to adjust the amount of inorganic salt so that it does not exceed the saturation concentration of salt in the aqueous reaction mixture.

The nature of the salt employed in the stage of the preparation of the dialkyl peroxydicarbonate is not particularly critical. In principle, any inorganic salt which does not interfere with the reaction for formation of the dialkyl peroxydicarbonate and which does not precipitate under the reaction conditions is suitable. Mention may be made, as non-limiting examples of such salts, of, for example, alkali metal and alkaline earth metal halides and in particular chlorides, in particular sodium chloride, but also alkali metal and alkaline earth metal sulphates, such as sodium sulphate, or alkali metal and alkaline earth metal nitrates, such as calcium nitrate.

The present invention also relates to an organic solution of dialkyl peroxydicarbonate in a water-insoluble organic solvent which is particularly suited for use in the aqueous suspension polymerization of halogenated monomers.

To this end, the invention relates to an organic solution of dialkyl peroxydicarbonate in a water-insoluble organic solvent, according to which this solvent is chosen from conventional chain-regulating agents for halogenated polymers.

The water-insoluble organic solvent is preferably chosen from conventional chain-regulating agents for polymers comprising fluorine and, in a more than preferred way, it is chosen from conventional chain-regulating agents for vinylidene fluoride polymers. In a very particularly preferred way, the water-insoluble organic solvent is diethyl carbonate.

The dialkyl peroxydicarbonate is preferably diethyl peroxydicarbonate.

In addition, the present invention relates to an organic solution of dialkyl peroxydicarbonate obtained by the preparation process forming the subject-matter of the invention.

The concentration of dialkyl peroxydicarbonate in the organic solution according to the invention is generally comprised between approximately 15 and approximately 40% by weight. The concentration of dialkyl peroxydicarbonate in the organic solution is preferably comprised between approximately 20 and approximately 35% by weight.

The invention also relates to a process for the preparation of halogenated polymers by aqueous suspension polymerization of halogenated monomers with the involvement of dialkyl peroxydicarbonate, according to which the dialkyl peroxydicarbonate is employed in the polymerization in the form of an organic solution in a water-insoluble organic solvent chosen from conventional chain-regulating agents for halogenated polymers.

The process for the preparation of halogenated polymers preferably applies to the preparation of polymers comprising fluorine and, in a more than preferred way, to the preparation of vinylidene fluoride polymers.

The water-insoluble organic solvent is preferably chosen from conventional chain-regulating agents for polymers comprising fluorine and, in a more than preferred way, it is chosen from conventional chain-regulating agents for vinylidene fluoride polymers. In a very particularly preferred way, the water-insoluble organic solvent is diethyl carbonate.

The dialkyl peroxydicarbonate is preferably diethyl peroxydicarbonate.

The concentration of dialkyl peroxydicarbonate in the solutions employed in the process for the preparation of halogenated polymers according to the invention is generally comprised between approximately 15 and approximately 40% by weight. Good results are obtained with solutions in which the concentration of dialkyl peroxydicarbonate is comprised between approximately 20 and approximately 35% by weight.

The organic solution of dialkyl peroxydicarbonate according to the invention is employed in amounts such that the dialkyl peroxydicarbonate is present in the polymerization mixture in usual amounts. The conventional amounts of the dialkyl peroxydicarbonate are from approximately 0.05 to 3% by weight with respect to the monomer employed and preferably from approximately 0.05 to 2% by weight. The amounts of the chain-regulating agent employed in the polymerization are conventionally from approximately 0.5 to 5% by weight with respect to the monomer employed. It may be necessary to add additional amounts of the chain-regulating agent in addition to those employed by the introduction of the organic solution of dialkyl peroxydicarbonate in the transfer agent.

The dialkyl peroxydicarbonates in organic solution are usually introduced at the beginning of the polymerization. However, it is understood that the dialkyl peroxydicarbonates in organic solution can be introduced, in all or in part, after the beginning of the polymerization (delayed). The delayed use of a part of the dialkyl peroxydicarbonate can be advantageous in improving the kinetics of the polymerization.

Apart from the distinguishing feature of the use of a dialkyl peroxydicarbonate in the form of an organic solution in a water-insoluble organic solvent according to the invention, the general conditions of the polymerization according to the process of the invention do not differ from those conventionally employed for the preparation of halogenated polymers, more particularly polymers comprising fluorine and in particular of vinylidene fluoride polymers, by aqueous suspension polymerization of halogenated monomers.

Aqueous suspension polymerization is understood to mean the polymerization with the involvement of oil-soluble initiators, in this case in particular dialkyl peroxydicarbonates, and in the presence of dispersing agent.

In the specific case of the preparation of vinylidene fluoride polymers, the dispersing agents are usually water-soluble cellulose derivatives, such as alkyl- and alkylhydroxyalkylcelluloses. The amount of dispersing agent employed generally varies between 0.01 and 0.5% by weight with respect to the monomer(s) employed. The best results are obtained when use is made of from 0.02 to 0.2% by weight thereof.

The polymerization temperature can be without distinction below or above the critical temperature of vinylidene fluoride (30.1° C.). When the temperature is below 30.1° C., the polymerization is carried out in a conventional aqueous suspension of liquid vinylidene fluoride under a pressure equal to the saturated vapour pressure of vinylidene fluoride. When the temperature is above 30.1° C., it is carried out in an aqueous suspension of gaseous vinylidene fluoride which is advantageously under high pressure. It is thus possible to carry out the process according to the invention at temperatures ranging from ambient temperature to approximately 110° C. Nevertheless, it is preferable to carry out the polymerization at a temperature above 30.1° C. According to a preferred embodiment of the process according to the invention, the polymerization of vinylidene fluoride is carried out at a temperature of between 35 and 100° C. and under initial pressures from approximately 55 to 200 bar. Of course, it is possible to increase the productivity of the reactors by carrying out, during polymerization, additional injections of monomer or of water or, during polymerization, raising the polymerization temperature.

The polymerization is generally carried out under batchwise conditions. It is generally carried out in vessel reactors provided with a blade, curved blade or turbine agitator.

At the end of polymerization, the vinylidene fluoride polymers obtained according to the process of the invention are isolated in a conventional way from their polymerization mixture, by a draining operation, followed by drying.

The invention also relates to halogenated polymers, characterized in that they have at least one of the following properties which is improved: a) thermal stability, b) purity.

Improved thermal stability is understood to mean that the yellowing index YI, measured following the Boy test, and/or the yellowing index YI (10 min), measured following the Boy test (10 min), are/is improved.

Improved purity is understood to mean that the halogenated polymer is characterized by a reduced content of metal ions.

The halogenated polymers are preferably polymers comprising fluorine and, in a more than preferred way, vinylidene fluoride polymers.

The invention also relates to the halogenated polymers obtained by the process according to the invention.

The terms used in the present text are defined hereinbelow.

Organic solution of dialkyl peroxydicarbonate in a water-insoluble organic solvent is understood to denote, for the purposes of the present invention, that the organic solution is composed essentially of the dialkyl peroxydicarbonate and of the water-insoluble organic solvent. It is thus devoid of any aqueous phase originating from the reaction mixture in which the dialkyl peroxydicarbonate was prepared.

Dialkyl peroxydicarbonate is understood to denote, for the purposes of the present invention, peroxydicarbonates in which the alkyl radicals comprise at least 2 carbon atoms and represent the ethyl, n-propyl, isopropyl, n-butyl, isobutyl, tert-butyl, n-octyl, 2-ethylhexyl, cyclohexyl, 4-tert-butylcyclohexyl, myristyl or cetyl radicals. Preference is given, among these, to diethyl and diisopropyl peroxydicarbonates. A very particularly preferred dialkyl peroxydicarbonate is diethyl peroxydicarbonate.

Water-insoluble organic solvent chosen from the chain-regulating agents is understood to denote, for the purposes of the present invention, the chain-regulating agents which are liquid and insoluble in water under standard conditions, that is to say at ambient temperature and at atmospheric pressure.

Water-insoluble is understood to mean more particularly a solubility in water at ambient temperature of less than 15% by weight. The solubility in water of the chain-regulating agents acting as solvent for the dialkyl peroxydicarbonate in the process of the invention preferably does not exceed 5% by weight and, in a more than preferred way, it does not exceed 3% by weight.

Mention may be made, inter alia, among the chain-regulating agents which can be used for the purposes of the invention, of halogenated derivatives, such as chloroform and trichlorofluoromethane, alkyl acetates, in which the alkyl comprises from 2 to 6 carbon atoms, and dialkyl carbonates.

Among the chain-regulating agents which can be used for the invention, dialkyl carbonates are preferred.

The most effective dialkyl carbonates, to which preference is consequently given, are those in which the alkyl groups comprise at most five carbon atoms. Mention may be made, as examples of such dialkyl carbonates, of dimethyl, diethyl, di(n-propyl), di(n-butyl), di(sec-butyl), diisobutyl, di(tert-butyl), di(n-pentyl), diisoamyl and dineopentyl carbonates.

A very particularly preferred dialkyl carbonate according to the invention is diethyl carbonate (solubility in water at ambient temperature: 1.9% by weight, relative density: 0.975).

Halogenated polymers is understood to denote, for the purposes of the present invention, both homopolymers and copolymers of halogenated monomers, in particular homopolymers of halogenated monomers, such as vinylidene fluoride, vinyl fluoride, trifluoroethylene, tetrafluoroethylene, chlorotrifluoroethylene, hexafluoropropylene, vinyl chloride or vinylidene chloride, as well as copolymers of these halogenated monomers and copolymers of one of these halogenated monomers with another monomer containing ethylenic unsaturation, such as ethylene, acrylic or methacrylic monomers, or vinyl acetate.

Polymers comprising fluorine is understood to denote, for the purposes of the present invention, both homopolymers and copolymers of monomers comprising fluorine, in particular homopolymers of vinylidene fluoride, of vinyl fluoride, of trifluoroethylene, of tetrafluoroethylene, of chlorotrifluoroethylene or of hexafluoropropylene, as well as copolymers of these monomers comprising fluorine, such as, for example, the copolymer of tetrafluoroethylene and of hexafluoropropylene, copolymers of vinylidene fluoride with another fluorinated monomer as defined above and copolymers of vinyl fluoride with another fluorinated monomer as defined above. The copolymers of one of the abovementioned monomers comprising fluorine with another monomer containing ethylenic unsaturation are also considered. The copolymer of tetrafluoroethylene and of ethylene and the copolymer of trifluoroethylene and of ethylene are examples thereof.

Vinylidene fluoride polymers is understood to denote, for the purposes of the present invention, both homopolymers of vinylidene fluoride and its copolymers with other monomers containing ethylenic unsaturation which are advantageously fluorinated. Mention may be made, as examples of fluorinated comonomers which can be used, of vinyl fluoride, trifluoroethylene, chlorotrifluoroethylene, tetrafluoroethylene and hexafluoropropylene. The copolymers obtained preferably comprise at least approximately 75% by weight of monomer units derived from vinylidene fluoride. The said thermoplastic copolymers advantageously exhibit a melting temperature at least equal to 130° C. and preferably at least equal to 150° C. and more particularly still to 165° C.

The process for the preparation of organic solutions of dialkyl peroxydicarbonates according to the invention provides solutions exhibiting numerous advantages. This is because, given that the impurities which appear during the preparation are water-soluble and are removed with the aqueous phase, the solutions obtained with a high yield are very pure. The solutions of dialkyl peroxydicarbonates obtained by the process according to the invention can be stored without disadvantage for relatively long time periods (several months) without significant loss in activity. Storage is generally carried out at low temperature, preferably at a temperature below −10° C., preferably in the region of 20° C. Relatively large amounts of the organic solution of dialkyl peroxydicarbonate, sufficient for a large number of polymerization cycles, can thus be prepared and subsequently stored, in order to be used as and when required. These solutions are ready-for-use and do not require the prior removal of the solvent, which has a role to play during the polymerization. The same solution can be used to feed several polymerization reactors. Finally, the solutions obtained can be transported and do not result in problems of deposits in the pipes.

The process for the preparation of halogenated polymers according to the invention has many advantages. In particular, it allows the feeding of the reactors to be automated. It results in an improvement in the reproducibility of the polymerization cycles. It also makes possible an increase in the productivity. The polymerization process of the invention also exhibits the advantage of involving a solution of the dialkyl peroxydicarbonate in a solvent which is itself a participant in the polymerization. Furthermore, the use of the dialkyl peroxydicarbonates in the form of an organic solution according to the invention makes it possible to obtain resins exhibiting either a better thermal stability or an increased purity or both, with respect to the resins obtained by preparing the dialkyl peroxydicarbonate "in situ".

EXAMPLE 1
Preparation of a Solution of Dialkyl Peroxydicarbonate 1300 g of demineralized water are introduced into a 4 liter autoclave placed under vacuum beforehand. After having regulated the temperature of the autoclave at +3° C., 111.7 g of 70% aqueous hydrogen peroxide solution and 600 g of ethyl chloroformate, cooled beforehand to between 0 and 5° C., are subsequently successively introduced into the aqueous solution, which is stirred by means of a curved blade agitator (speed of 400 revolutions/minute), while the autoclave is still under vacuum. The piping conveying the ethyl chloroformate is then rinsed with 500 g of demineralized water and the speed of stirring is increased to 750 revolutions/minute. The autoclave is subsequently brought to atmospheric pressure before slowly introducing 780 ml of a 6N sodium hydroxide solution over 1 hour. The temperature is regulated at +3° C. ±2° C. throughout the introduction of the sodium hydroxide. After the end of the introduction of the sodium hydroxide, the reaction mixture is kept stirring for 10 minutes. The temperature of the autoclave is subsequently indexed at +1° C. and, under a speed of stirring reduced to 200 revolutions/minute, 1300 g of diethyl carbonate, cooled beforehand to between 0 and 5° C., are introduced. After having kept the reaction mixture stirring at 750 revolutions/minute for 10 minutes, the stirring is then halted and separation by settling is allowed to take place for 30 minutes. The autoclave is subsequently brought back to atmospheric pressure and the organic and aqueous phases are withdrawn. 1631 g of organic solution are thus collected, which solution has a diethyl peroxydicarbonate assay of 245 g/kg, i.e. a yield of 85% with respect to the hydrogen peroxide. The diethyl peroxydicarbonate solution thus produced is stored under cold conditions (approximately −20° C.) for the purpose of its subsequent use.

EXAMPLE 2
Preparation of a Halogenated Polymer 19 kg of demineralized water and 270 g of a 15 g/kg aqueous ethylhydroxypropylcellulose solution are successively introduced into a 30.8 liter reactor which is vigorously stirred and equipped with a jacket. The greater part of the oxygen present in the reactor is removed by placing under a vacuum of 40 mbar (at 15° C.) three times with, after the first two of these operations, repressurizing with 1 bar of nitrogen. 82 g of a 24.5% by weight solution of diethyl peroxydicarbonate in diethyl carbonate are then introduced under vacuum. An additional 131 g of pure diethyl carbonate are added. A single charge of 8 kg of vinylidene fluoride is subsequently introduced and then the reactor is gradually heated until a first stationary temperature phase of 42° C. is reached, for a duration of approximately 1 hour 30 minutes. The temperature is subsequently brought to 61° C. and is maintained there for approximately 1 hour 45 minutes. At the end of polymerization, the aqueous suspension is degassed (the pressure being lowered to atmospheric pressure). The polymer collected is washed and dried to constant weight. The total duration of the polymerization is 3 hours 50 minutes. The degree of conversion measured is 94%.

EXAMPLE 3
Properties of the Halogenated Polymer Obtained in Example 2

The MFI (Melt Flow Index) of the polymer obtained, measured according to ISO Standard 1133 at a temperature of 230° C. and under a weight of 2.16 kg, is 12 g/10 minutes. The yellowing index YI, measured following the Boy test, and the yellowing index YI (10 min), measured following the Boy test, 10 min, are respectively 11 and 20. The Boy test and the measurement method for determining the yellowing index YI are described hereinbelow. The content of metal ions and in particular the content of sodium ions is less than 1 mg/kg of poly(vinylidene fluoride). The method of determination of the content of metal ions is described hereinbelow.

Description of the Thermal Stability Test (Boy Test)

The poly(vinylidene fluoride) is subjected to a thermal and mechanical stress during injection of a test specimen with an injection moulding machine. The article to be injected, with dimensions of 60×40×4 mm, is injected via a shell (31.5×0.8 mm). The mould is connected to a thermal regulation system. The temperature of the mould is regulated at 60±2° C. The injection moulding machine used is a Boy 15 S injection moulding machine, which is characterized by a closing force of 22 tonnes, a cylinder with a diameter of 22 mm, an open nozzle with a diameter of 2.1 mm as injection nose, a non-return valve composed of 3 V-shaped channels, a screw characterized by an L/D ratio of 20, 3 zones (12D/4D/4D) and a compression ratio of 1.9. Two independent heating resistance elements are placed on the barrel (zones 1 and 2) and two resistance elements coupled to the zone of the non-return valve and the injection nose (zone 3). The temperatures of these 3 heating zones are, in order, 190° C., 220° C. and 265° C. The residence time in the barrel is of the order of 5 minutes. The thermal effect can be increased by maintaining the hot molten polymer in the barrel of the machine, the injection cycle being interrupted for 10 minutes (Boy test, 10 min).

Description of the Measurement Method for the Determination of the Yellowing Index YI The yellowing index YI of the samples is determined according to ASTM Standard D-1925 by means of a Hunterlab "Ultrascan" spectrocolorimeter regularly calibrated by virtue of 3 Hunterlab colorimetric calibrating standards (white, black, grey). The measurement reference system is the CIELAB 1976, the illuminant is D65 from the CIE, the spectral band analysed is from 400 to 700 nm, the spectral measurement interval is 5 nm, the diameter of the range examined is 0.95 cm, the standard observer is at 10° and observation is carried out under an angle of 8°.

Description of the Method for the Determination of the Content of Metal Ions

The content of metal ions, in particular the content of sodium ions, expressed as mg/kg of poly(vinylidene fluoride), is measured by atomic absorption spectrometry in an air-acetylene flame (F-AAS) at a wavelength of 589.0 nm. Before analysis, the sample is first subjected to mineralization by sulphuric acid in a platinum dish, followed by calcination at 580° C., the ash being taken up in 5 mol/liter hydrochloric acid and made up to volume in the presence of caesium (spectral gauge).

EXAMPLE 4 (COMPARATIVE)

Properties of a Halogenated Polymer Obtained with the Involvement of a Dialkyl Peroxydicarbonate Prepared "in situ"

By way of comparison, the polymerization of vinylidene fluoride was repeated under the same conditions as in Example 2, except that the appropriate amount of diethyl peroxydicarbonate is first synthesized "in situ" in the polymerization reactor. Thus, 19 kg of demineralized water, 9 g of sodium hydroxide, 38.3 g of 10% aqueous hydrogen peroxide solution and 270 g of a 15 g/kg aqueous ethylhydroxypropylcellulose solution are successively introduced into a 30.8 liter reactor which is vigorously stirred and equipped with a jacket. After deaerating the autoclave by placing under vacuum and repressurizing with nitrogen, 24.5 g of ethyl chloroformate and 190 g of diethyl carbonate, as chain-regulating agent, are added. A single charge of 8 kg of vinylidene fluoride is subsequently introduced and then the reactor is gradually heated until a first stationary temperature phase of 42° C. is reached, for a duration of approximately 2 hours. The temperature is subsequently brought to 61° C. and is maintained there for approximately 2 hours. At the end of polymerization, the aqueous suspension is degassed (the pressure being lowered to atmospheric pressure). The polymer collected is washed and dried to constant weight. The total duration of the polymerization is 4 hours 40 minutes. The degree of conversion measured is 94%.

The MFI (Melt Flow Index) of the polymer obtained in Example 4, measured according to ISO Standard 1133 at a temperature of 230° C. and under a weight of 2.16 kg, is 10 g/10 minutes. The yellowing index YI, measured following the Boy test, and the yellowing index YI (10 min), measured following the Boy test, 10 min, are 13 and 29 respectively. The content of metal ions and in particular the content of sodium ions is 2 mg/kg of poly(vinylidene fluoride).

From the comparison of the results, it is apparent that the use of diethyl peroxydicarbonate in solution in diethyl carbonate (according to the invention) in the polymerization of vinylidene fluoride gives rise to the preparation of vinylidene fluoride polymers which are significantly more stable thermally and which have a higher ionic purity (Examples 2 and 3) than those obtained with the involvement of diethyl peroxydicarbonate prepared "in situ" (Comparative Example 4).

What is claimed is:

1. A process for the preparation of an organic solution of dialkyl peroxydicarbonate, by reacting an alkyl haloformate in water with an inorganic peroxide to form the dialkyl peroxydicarbonate and extracting the formed dialkyl peroxydicarbonate with a water-insoluble organic solvent chosen from dialkyl carbonates to obtain the organic solution of dialkyl peroxydicarbonate in this solvent.

2. The process for the preparation of an organic solution of dialkyl peroxydicarbonate according to claim 1, wherein the dialkyl carbonates are those in which the alkyl groups comprise at most five carbons.

3. The process for the preparation of an organic solution of dialkyl peroxydicarbonate according to claim 2 wherein the dialkyl carbonate is diethyl carbonate.

4. Process for the preparation of an organic solution of dialkyl peroxydicarbonate according to claim 1, wherein the dialkyl peroxydicarbonate is diethyl peroxydicarbonate.

5. An organic solution of dialkyl peroxydicarbonate in a water-insoluble organic solvent, wherein the solvent is chosen from dialkyl carbonates.

6. The organic solution of dialkyl peroxydicarbonate according to claim 6, wherein the dialkyl carbonates are those in which the alkyl groups comprise at most five carbons atoms.

7. The organic solution of dialkyl peroxydicarbonate according to claim 6, wherein the dialkyl carbonate is diethyl carbonate.

8. The organic solution of dialkyl peroxydicarbonate according to claim 5, wherein the dialkyl peroxydicarbonate is diethyl peroxydicarbonate.

* * * * *